United States Patent
Gamache et al.

(10) Patent No.: US 6,872,382 B1
(45) Date of Patent: Mar. 29, 2005

(54) USE OF SELECTIVE PDE IV INHIBITORS TO TREAT DRY EYE DISORDERS

(75) Inventors: Daniel A. Gamache, Arlington, TX (US); John M. Yanni, Burleson, TX (US)

(73) Assignee: Alcon, Inc., Hunenberg (CH)

(*) Notice: Subject to any disclaimer, the term of this patent is extended or adjusted under 35 U.S.C. 154(b) by 515 days.

(21) Appl. No.: 10/150,193

(22) Filed: May 17, 2002

Related U.S. Application Data

(60) Provisional application No. 60/292,499, filed on May 21, 2001.

(51) Int. Cl.$^7$ .............................................. A61K 31/74
(52) U.S. Cl. ................................................... 424/78.04
(58) Field of Search ...................................... 424/78.04

(56) References Cited

U.S. PATENT DOCUMENTS

| | | | |
|---|---|---|---|
| 3,991,759 A | 11/1976 | Urquhart | 128/260 |
| 4,131,651 A | 12/1978 | Shah et al. | 424/78 |
| 4,370,325 A | 1/1983 | Packman | 424/245 |
| 4,409,205 A | 10/1983 | Shively | 424/78 |
| 4,744,980 A | 5/1988 | Holly | 424/78 |
| 4,753,945 A | 6/1988 | Gilbard et al. | 514/263 |
| 4,804,539 A | 2/1989 | Guo et al. | 424/450 |
| 4,818,537 A | 4/1989 | Guo | 424/427 |
| 4,883,658 A | 11/1989 | Holly | 424/80 |
| 4,914,088 A | 4/1990 | Glonek et al. | 514/76 |
| 4,956,348 A * | 9/1990 | Gilbard et al. | 514/47 |
| 4,966,773 A | 10/1990 | Gressel et al. | 424/489 |
| 4,975,428 A | 12/1990 | Shell | 514/230.5 |
| 5,036,046 A | 7/1991 | Neufeld et al. | 514/12 |
| 5,041,434 A | 8/1991 | Lubkin | 514/182 |
| 5,075,104 A | 12/1991 | Gressel et al. | 424/78.04 |
| 5,174,988 A | 12/1992 | Mautone et al. | 424/45 |
| 5,278,151 A | 1/1994 | Korb et al. | 514/76 |
| 5,290,572 A | 3/1994 | MacKeen | 424/602 |
| 5,294,607 A | 3/1994 | Glonek et al. | 514/76 |
| 5,371,108 A | 12/1994 | Korb et al. | 514/762 |
| 5,393,788 A | 2/1995 | Bender et al. | 514/616 |
| 5,403,841 A | 4/1995 | Lang et al. | 514/226.8 |
| 5,449,686 A | 9/1995 | Christensen, IV et al. | 514/330 |
| 5,491,147 A | 2/1996 | Boyd et al. | 514/247 |
| 5,578,586 A | 11/1996 | Glonek et al. | 514/76 |
| 5,605,914 A | 2/1997 | Muller | 514/339 |
| 5,620,921 A | 4/1997 | Sullivan | 514/178 |
| 5,677,335 A | 10/1997 | Robertson et al. | 514/521 |
| 5,696,166 A | 12/1997 | Yanni et al. | 514/573 |
| 5,712,298 A | 1/1998 | Amschler | 514/352 |
| 5,800,807 A | 9/1998 | Hu et al. | 424/78.04 |
| 5,958,912 A | 9/1999 | Sullivan | 514/177 |
| 6,071,904 A | 6/2000 | Ali et al. | 514/222.8 |

FOREIGN PATENT DOCUMENTS

| | | |
|---|---|---|
| AU | 9474907 | 7/1994 |
| EP | 0 738 715 A3 | 6/1998 |
| WO | WO 92/00968 | 1/1992 |
| WO | WO 95/01338 | 1/1995 |
| WO | WO 95/09836 | 4/1995 |
| WO | WO 95/27692 | 10/1995 |
| WO | WO 95/31211 | 11/1995 |
| WO | WO 95/35283 | 12/1995 |
| WO | WO 95/35284 | 12/1995 |
| WO | WO 96/00218 | 1/1996 |
| WO | WO 96/01825 | 1/1996 |
| WO | WO 96/32105 | 10/1996 |
| WO | WO 96/00215 | 11/1996 |
| WO | WO 96/36595 | 11/1996 |
| WO | WO 99/50270 | 10/1999 |
| WO | WO 00/03705 | 1/2000 |
| WO | WO 00/43000 | 7/2000 |
| WO | WO 00/61168 | 10/2000 |
| WO | WO 00/64863 | 11/2000 |
| WO | WO/03/03749 | * 5/2003 |
| WO | WO 03/099278 | 12/2003 |
| WO | WO 03/099334 | 12/2003 |

OTHER PUBLICATIONS

Ballestas et al., "Elevation of Cyclic AMP Levels in Astrocytes Antagonizes Cytokine–Induced Adhesion Molecule Expression," *J. of Neurochemistry*, vol. 69(4), pp. 1438–1448 (1997).

Blease et al., "Modulation of cell adhesion molecule expression and function on human lung microvascular endothelial cells by inhibition of phosphodiesterases 3 and 4," *British J. of Pharmacology*, vol. 124, pp. 229–237 (1998).

Bode et al., "Distinct Profiles of Phosphodiesterase Isozymes in Cultured Cells Derived from Nonpigmented and Pigmented Ocular Ciliary Epithelium," vol. 267 (3), pp. 1286–1291 (1993).

Bruynzeel et al., "Pentoxifylline Inhibits Human T–cell Adhesion to Dermal Endothelial Cells," *Arch. Dermatol Res.*, pp. 189–193 (1997).

Corey et al., "Total Synthesis and Biological Activity of Lactacystin, Omuralide and Analogs," *Chem. Pharm. Bull.*, vol. 47(1), pp. 1–10 (1999).

Driessens et al., "Activation of G–Proteins with $AIF_4$ Induces LFA–1–Mediated Adhesion of T–Cell Hybridoma Cells to ICAM–1 by Signal Pathways that Differ from Phorbol Ester and Manganese–Induced Adhesion," *Experimental Cell Research*, vol. 231, pp. 242–250 (1997).

Gilbard et al., "Stimulation of Tear Secretion by Topical Agents," *Investigative Ophthalmology & Vis. Science*, vol. 31(7), pp. 1381–1388 (1990).

Hayashi et al., "Butein (3,4,2',4'-tetrahydroxychalcone) ameliorates experimental anti–glomerular basement membrane antibody–associated glomerulonephritis (3)," *European J. of Pharmacology*, vol. 316, pp. 297–306 (1996).

(Continued)

Primary Examiner—Carlos A. Azpuru
(74) Attorney, Agent, or Firm—Patrick M. Ryan

(57) ABSTRACT

Selective PDE-IV inhibitors are useful for treating dry eye disorders and other disorders requiring the wetting of the eye.

4 Claims, No Drawings

OTHER PUBLICATIONS

Knorr et al., "The Lymphocyte Function–associated Antigen 1 I Domain is a Transient Binding Module for Intercellular Adhesion Molecule (ICAM)–1 and ICAM–3 in Hydrodynamic Flow," *J. Exp. Medicine,* vol. 186(5), pp. 719–730 (1997).

Lemp et al., "Report of the National Eye Institute/Industry Workshop on Clinical Trials in Dry Eyes," *CLAO Journal,* vol. 21(4), pp. 221–231 (1995).

Liefner et al., "Concentration–dependent effects of pentoxifylline on mirgration and myelin phagocytosis by macrophages," *J. of Neuroimmunology,* vol. 89, pp. 97–103 (1998).

McCulley et al., "Tear Film Structure and Dry Eye," *Contactologia,* vol. 20, pp. 145–149 (1998).

Marsh et al., "Topical Nonpreserved Methylprednisolone Therapy for Keratoconjunctivitis Sicca in Sjogren Syndrome," *Ophthalmology,* vol. 106(4), pp. 811–816 (1999).

Modur et al., "Endothelial Cell Inflammatory Responses to Tumor Necrosis Factor," *J. of Biological Chemistry,* vol. 271(22), pp. 13094–13102 (1996).

Morandini et al., "Action of cAMP in expression and release of adhesion molecules in human endothelial cells," *American J. of Physiology,* vol. 270(3 Pt 2), pp. H807–H816 (1996).

Newsholme et al., "cAMP–Specific Phosphodiesterase Inhibitor, Rolipram, Reduces Eosinophil Infiltration Evoked by Leukotrienes or by Histamine in Guinea Pig Conjunctiva," *Inflammation,* vol. 17(1), pp. 25–31 (1993).

Poggi et al., "Dissection of lymphocyte function–associated antigen 1–dependent adhesion and signal transduction in human natural killer cells shown by the use of cholera or pertussis toxin," *Eur. J. Immunology,* vol. 26, pp. 967–975 (1996).

Rieckmann et al., "Pentoxifylline, a phosphodiesterase inhibitor, induces immune deviation in patients with multiple sclerosis," *J. of Neuroimmunology,* vol. 64, pp. 193–200 (1996).

Shafren et al., "Coxackievirus A21 Binds to Decay–Accelerating Factor but Requires Intercellular Adhesion Molecule 1 for Cell Entry," *J. of Virology,* vol. 71 (6), pp. 4736–4743 (1997).

Shine et al., "Keratoconjunctivitis Sicca Associated with Meibornian Secretion Polar Lipid Abnormality," *Arch. Ophthalmol.* vol. 116, pp. 849–852 (1998).

Soucy et al., "A Novel and Efficient Synthesis of a Highly Active Analogue of clasto–Lactacystin β–Lactone," J. Am. Chem. Soc, vol. 121, pp. 9967–9976 (1999).

Tauber et al., "A Dose–Ranging Clinical Trial to Assess the Safety and Efficacy of Cyclosporine Ophthalmic Emulsion in Patients with Keratoconjunctivitis Sicca," Lacrimal Gland, Tear Film and Dry Eye Syndromes 2, edited by Sullivan et al., Plenum Press, New York, pp. 969–972 (1998).

* cited by examiner

USE OF SELECTIVE PDE IV INHIBITORS TO TREAT DRY EYE DISORDERS

This application claims priority to U.S. Provisional Application Ser. No. 60/292,499, filed May 21, 2001.

The present invention is directed to the treatment of dry eye disorders. In particular, the present invention is directed to the use of PDE IV inhibitors in the treatment of dry eye and other disorders requiring the wetting of the eye in mammals.

BACKGROUND OF THE INVENTION

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, *Report of the National Eye Institute/Industry Workshop on Clinical Trials in Dry Eyes, The CLAO Journal*, volume 21, number 4, pages 221–231 (1995)).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g., McCulley and Shine, *Tear film structure and dry eye, Contactologia*, volume 20(4), pages 145–49 (1998); and Shine and McCulley, *Keratoconjunctivitis sicca associated with meibomian secretion polar lipid abnormality, Archives of Ophthalmology*, volume 116(7), pages 849–52 (1998). Examples of phospholipid compositions for the treatment of dry eye are disclosed in U.S. Pat. Nos. 4,131,651 (Shah et al.), 4,370,325 (Packman), 4,409,205 (Shively), 4,744,980 and 4,883,658 (Holly), 4,914,088 (Glonek), 5,075,104 (Gressel et al.), 5,278,151 (Korb et al.), 5,294,607 (Glonek et al.), 5,371,108 (Korb et al.) and 5,578,586 (Glonek et al.). U.S. Pat. No. 5,174,988 (Mautone et al.) discloses phospholipid drug delivery systems involving phospholipids, propellants and an active substance.

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day.

Such an undertaking is not only cumbersome and time consuming, but is also potentially very expensive. Transient symptoms of dry eye associated with refractive surgery have been reported to last in some cases from six weeks to six months or more following surgery.

Aside from efforts directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye conditions in post-menopausal women; U.S. Pat. No. 5,290,572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Some recent literature reports suggest that patients suffering from dry eye syndrome disproportionately exhibit the hallmarks of excessive inflammation in relevant ocular tissues, such as the lacrimal and meibomian glands. The use of the following types of pharmaceutically active compounds to treat dry eye patients has been disclosed: steroids [e.g. U.S. Pat. No. 5,958,912; Marsh, et al., *Topical non-preserved methylprednisolone therapy for keratoconjunctivitis sicca in Sjogren syndrome, Ophthalmology*, 106(4): 811–816 (1999); Pflugfelder, et. al. U.S. Pat. No. 6,153,607], cytokine release inhibitors (Yanni, J. M.; et. al. WO 0003705 A1), cyclosporine A [Tauber, *J. Adv. Exp. Med. Biol.* 1998, 438 (Lacrimal Gland, Tear Film, and Dry Eye Syndromes 2), 969], and 15-HETE (Yanni et al., U.S. Pat. No. 5,696,166).

Phosphodiesterase enzymes catalyze the degradation of cyclic nucleotides such as cyclic adenosine monphosphate (cAMP) and cyclic guanosine monophosphate (cGMP). Both cAMP and cGMP have been shown to stimulate lacrimal gland secretion and increase tear volume (Gilbard J P, Rossi S R, Heyda K G, and Dartt D A. Stimulation of tear secretion by topical agents that increase cyclic nucleotide levels. IOVS 31(7):1381–8, 1990). Therefore, nonspecific inhibitors of phosphodiesterases have, been proposed to be therapeutically useful in dry eye by stimulating tear production. However, phosphodiesterase enzymes which have the capacity to suppress inflammation may treat dry eye by virtue of an anti-inflammatory property. Phosphodiesterase type-IV (PDE-IV) is the predominant cyclic nucleotide hydrolyzing enzyme found in inflammatory leukocytes, such as mast cells, neutrophils, monocytes and T-lymphocytes. The substrate for PDE-IV is cAMP, a known anti-inflammatory second messenger. Elevated cAMP levels inhibit leukocyte function and suppress cytokine production in a variety of cells. PDE-IV hydrolyzes the anti-inflammatory nucleotide, cAMP, thereby reducing its intracellular level. PDE-IV inhibitors prevent the breakdown of cAMP and thereby exhibit antiinflammatory activity. Therefore, PDE-IV inhibitors would be useful therapeutic agents in reducing inflammatory processes contributing to the manifestations of dry eye.

SUMMARY OF THE INVENTION

The present invention is directed to methods for the treatment of dry eye and other disorders requiring the wetting of the eye, including symptoms of dry eye associated with refractive surgery such as LASIK surgery. According to the methods of the present invention, selective PDE-IV inhibitors are administered to a patient suffering from dry eye or other disorders requiring wetting of the eye. The selective PDE-IV inhibitors are preferably administered topically to the eye.

DETAILED DESCRIPTION OF THE INVENTION

PDE-IV belongs to a family of cyclic nucleotide hydrolyzing enzymes which are distinguished by substrate preference, tissue distribution and biochemical and pharmacological properties. PDE-I enzymes are Calcium/calmodulin dependent, PDE-II enzymes are cGMP-stimulated, PDE-III enzymes are cGMP inhibited, PDE-IV enzymes are CAMP specific, PDE-V are cGMP specific, PDE-VI exists only in the retina and PDE-VII enzymes have a high affinity for cAMP. Selective inhibitors of individual phosphodiesterase enzymes can be identified in in vitro enzyme assays using known techniques. Since PDE-IV activity controls the levels of cAMP in inflammatory cells, inhibitors of this enzyme have anti-inflammatory activity. Inhibitors of phosphodiesterases vary in selectivity and specificity for individual enzymes and therefore can possess diverse pharmacological and toxicological properties. This invention applies to highly selective inhibitors of the type-IV enzyme with the primary biological effect being suppression of inflammation. As used herein, "selective PDE-IV inhibitor" means a non-steroid compound that selectively inhibits type IV phosphodiesterase enzyme activity (relative to activities of other types of phosphodiesterase enzymes). As used herein, a compound that selectively inhibits type IV phosphodiesterase enzyme activity is a compound that is at least ten times more potent at inhibiting type IV phosphodiesterase enzyme activity than any other type of phosphodiesterase enzyme activity. Preferred PDE-IV inhibitors for use in the present invention are at least one thousand times more potent at inhibiting type IV phosphodiesterase enzyme activity than any other type of phosphodiesterase enzyme activity.

Selective PDE-IV inhibitors are known. Examples of selective PDE-IV inhibitors useful in the methods of the present invention include, but are not limited to: 2-(4-ethoxycarbonylaminobenzyl)-6-(3,4-dimethoxyphenyl)-2,3,4,5-tetrahydro-pyridazin-3-one and the related compounds disclosed in EP 0 738 715; 3-[3-(cyclopentyloxy)-4-methoxybenzyl]-6(ethylamino)-8-isopropyl-3H-purine hydrochloride (also known as V-11294A) and the related compounds disclosed in WO 96/00218; 8-methoxyquinoline-5-[N-(2,5-dichloropyridin-3-yl)] carboxamide (also known as D4418) and related compounds disclosed in WO 96/36595; the compounds disclosed in U.S. Pat. No. 5,605,914; cipamfylliine (also known as BRL-61063); ariflo (also known as SB-207499); and compounds disclosed in WO 99/50270.

According to the methods of the present invention, a composition comprising one or more selective PDE-IV inhibitors and a pharmaceutically acceptable carrier for topical ophthalmic administration or implantation into the conjunctival sac or anterior chamber of the eye is administered to a mammal in need thereof. The compositions are formulated in accordance with methods known in the art for the particular route of administration desired.

The compositions administered according to the present invention comprise a pharmaceutically effective amount of one or more selective PDE-IV inhibitors. As used herein, a "pharmaceutically effective amount" is one which is sufficient to reduce or eliminate signs or symptoms of dry eye or other disorders requiring the wetting of the eye. Generally, for compositions intended to be administered topically to the eye in the form of eye drops or eye ointments, the total amount of selective PDE-IV inhibitor will be about 0.001 to 1.0% (w/v).

Preferably, the compositions administered according to the present invention will be formulated as solutions, suspensions and other dosage forms for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions. Suspensions may be preferred for selective PDE-IV inhibitors which are sparingly soluble in water.

The compositions administered according to the present invention may also include various other ingredients, including but not limited to surfactants, tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150–450 mOsm, preferably 250–350 mOsm).

An appropriate buffer system: (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 6–7.5.

Compositions formulated for the treatment of dry eye-type diseases and disorders may also comprise aqueous carriers designed to provide immediate, short-term relief of dry eye-type conditions. Such carriers can be formulated as a phospholipid carrier or an artificial tears carrier, or mixtures of both. As used herein, "phospholipid carrier" and "artificial tears carrier" refer to aqueous compositions which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide the appropriate delivery vehicle for the topical administration of an effective amount of one or more PDE IV inhibitors. Examples or artificial tears compositions useful as artificial tears carriers include, but are not limited to, commercial products, such as Tears Naturale®, Tears Naturale II®, Tears Naturale Free®, and Bion Tears® (Alcon Laboratories, Inc., Fort Worth, Tex.). Examples of phospholipid carrier formulations include those disclosed in U.S. Pat. Nos. 4,804,539 (Guo et al.), 4,883,658 (Holly), 4,914,088 (Glonek), 5,075,104 (Gressel et al.), 5,278,151 (Korb et al.), 5,294,607 (Glonek et al.), 5,371,108 (Korb et al.), 5,578,586 (Glonek et al.); the foregoing patents are incorporated herein by reference to the extent they disclose phospholipid compositions useful as phospholipid carriers of the present invention.

Other compounds designed to lubricate, "wet," approximate the consistency of endogenous tears, aid in natural tear build-up, or otherwise provide temporary relief of dry eye symptoms and conditions upon ocular administration the eye are known in the art. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoises ("cps").

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The preferred compositions of the present invention are intended for administration to a human patient suffering from dry eye or symptoms of dry eye. Preferably, such compositions will be administered topically. In general, the doses used for the above described purposes will vary, but will be in an effective amount to eliminate or improve dry eye conditions. Generally, 1–2 drops of such compositions will be administered from once to many times per day.

A representative eye drop formulation is provided in Example 1 below.

| Ingredient | Amount (% w/v) |
|---|---|
| Selective PDE-IV inhibitor | 0.001–1.0 |
| Polyoxyl 40 Stearate | 0.1 |
| Boric Add | 0.25 |
| Sodium Chloride | 0.75 |
| Disodium Edetate | 0.01 |
| Polyquaternium-1 | 0.001 |
| NaOH/HCl | q.s., pH = 7.4 |
| Purified Water | q.s. 100% |

The above composition is prepared by the following method. The batch quantities of boric acid, sodium chloride, disodium edetate, and polyquaternium-1 are weighed and dissolved by stirring in 90% of the batch quantity of purified water. The pH is adjusted to 7.4±0.1 with NaOH and/or HCl. The batch quantity of the selective PDE IV inhibitor as a stock solution is measured and added. Purified water is added to q.s. to 100%. The mixture is stirred for five minutes to homogenize and then filtered through a sterilizing filter membrane into a sterile recipient.

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A method for the treatment of dry eye which comprises administering to a mammal a composition comprising a pharmaceutically acceptable carrier and a pharmaceutically effective amount of one or more selective PDE-IV inhibitors.

2. The method of claim 1 wherein the pharmaceutically effective amount of one or more selective PDE IV inhibitors is 0.001–1.0% (w/v).

3. The method of claim 1 wherein the composition is topically administered to the eye.

4. The method of claim 1 wherein the dry eye is associated with refractive surgery.

* * * * *